(12) United States Patent
Doyle et al.

(10) Patent No.: US 11,998,476 B2
(45) Date of Patent: Jun. 4, 2024

(54) CUP SUPPORTS AND METHODS OF USING SAME

(71) Applicant: Kristin Johnson Doyle, Atlanta, GA (US)

(72) Inventors: Kristin Johnson Doyle, Atlanta, GA (US); James Atticus Ferguson, Atlanta, GA (US)

(73) Assignee: Kristin Johnson Doyle, Atlanta, GA (US)

( * ) Notice: Subject to any disclaimer, the term of this patent is extended or adjusted under 35 U.S.C. 154(b) by 689 days.

(21) Appl. No.: 17/158,162

(22) Filed: Jan. 26, 2021

(65) Prior Publication Data

US 2022/0142809 A1 May 12, 2022

Related U.S. Application Data

(60) Provisional application No. 63/110,635, filed on Nov. 6, 2020.

(51) Int. Cl.
*A61F 5/455* (2006.01)
(52) U.S. Cl.
CPC .................................... *A61F 5/455* (2013.01)
(58) Field of Classification Search
CPC ...................................................... A61F 5/455
See application file for complete search history.

(56) References Cited

U.S. PATENT DOCUMENTS

| | | | |
|---|---|---|---|
| D306,648 S | 3/1990 | Jones | |
| D334,693 S | 4/1993 | Burke | |
| D335,176 S | 4/1993 | Jones | |
| D335,180 S | 4/1993 | Jones et al. | |
| D341,883 S | 11/1993 | Jones et al. | |
| 5,492,220 A | 2/1996 | Estay | |
| D398,993 S | 9/1998 | Jones | |
| D399,007 S | 9/1998 | Jones | |
| D408,913 S | 4/1999 | Jones | |
| 6,013,230 A | 1/2000 | Kuchar | |
| D442,836 S | 5/2001 | Hunter | |
| D449,685 S | 10/2001 | Morrison | |
| D456,898 S | 5/2002 | Yang | |
| D458,523 S | 6/2002 | Newton, Sr. | |
| D488,691 S | 4/2004 | Ziems | |
| 6,719,951 B1 | 4/2004 | Griffith | |
| D496,570 S | 9/2004 | Wolf | |
| 6,973,678 B2 | 12/2005 | Jones | |

(Continued)

FOREIGN PATENT DOCUMENTS

WO 99/52442 10/1999

OTHER PUBLICATIONS

"Azer Scientific Choyce Clean Catch Urine Collection Kit," Azer Scientific, available online at: https://www.fishersci.com/shop/products/azer-choyce-clean-catch-urine-collection-kit-2/p-4667980, accessed from Internet on Feb. 23, 2021, 1 page.

(Continued)

*Primary Examiner* — Yi-Shan Yang
*Assistant Examiner* — Joseph A Tombers
(74) *Attorney, Agent, or Firm* — Kristin Johnson Doyle

(57) ABSTRACT

Cup supports having a head portion defining an aperture for receiving a specimen cup for the collection of a liquid and a handle portion extending from the head portion. The head portion and the handle portion can be integrally formed, and in some embodiments the cup support is adapted to absorb liquid that impinges on it during use.

19 Claims, 28 Drawing Sheets

(56) References Cited

U.S. PATENT DOCUMENTS

| | | |
|---|---|---|
| 7,128,352 B1 | 10/2006 | Phippen |
| D593,206 S | 5/2009 | Kopoian |
| D618,523 S | 6/2010 | Jalet et al. |
| 8,091,848 B1 | 1/2012 | Reed |
| D654,598 S | 2/2012 | Hooper |
| 8,465,440 B1 | 6/2013 | Grayson |
| D706,947 S | 6/2014 | Hooper |
| D753,452 S | 4/2016 | Merritt |
| D773,657 S | 12/2016 | Meloff |
| D775,270 S | 12/2016 | Moffat |
| 9,662,094 B2 | 5/2017 | Meloff |
| D833,839 S | 11/2018 | Scano |
| D895,796 S | 9/2020 | Washington |
| D953,524 S | 5/2022 | Green |
| 2002/0179794 A1 | 12/2002 | Yang |
| 2008/0140032 A1 | 6/2008 | O'Malley |
| 2009/0076413 A1 | 3/2009 | Robles |
| 2009/0209881 A1 | 8/2009 | Willcocks |
| 2010/0174209 A1 | 7/2010 | Fleshman |
| 2011/0071434 A1 | 3/2011 | Higgins |
| 2016/0089118 A1 | 3/2016 | Petersilia |

OTHER PUBLICATIONS

"Medegen Medical Products LLC Specimen Cup Holder Helpful Hand™ White, Plastic, NonSterile For ClikSeal™, Gent-L-Kare™, Standard Specimen Containers," Medigen Medical Products LLC, available online at: https://www.devineexpress.com/products/2270-medegen-medical-products-llc-specimen-cup-holder-helpful-hand-white-plastic-nonsterile-for-clikseal-gent-l-kare-standard-specimen-containers?variant=15391024545835&cmp_id=1705750308&adg_id=66027571625&kwd=&device=c&gclid=Cj0KCQiA48j9BRC-ARIsAMQu3WS1OzBDfrXlECh8oZwbuRVCjqEEBRdB267keQVJ3gUy9ASROWMfvJcaAqqdEALw_wcB, accessed from Internet on Feb. 25, 2021, 2 pages.

"100 Pack Disposable Plastic Urine Cups, 50ML Tests Cup Urine Specimen Container for Ovulation Test/Pregnancy Test/pH Test/Ketone Test," available online at: https://www.amazon.com/Disposable-Specimen-Container-Ovulation-Pregnancy/dp/B083W9DDM7, accessed from Internet on Feb. 25, 2021, 6 pages.

"Medegen Medical Products MDG 02270 Specimen Cup Holder with White Cardboard, 125 Per Sleeve—8 Sleeve Per Case," Medigen Medical Products LLC, available online at: https://www.walmart.com/ip/Medegen-Medical-Products-MDG-02270-Specimen-Cup-Holder-with-White-Cardboard-44-125-Per-Sleeve-8-Sleeve-Per-Case/614250625, accessed from Internet on Feb. 25, 2021, 3 pages.

CUP SUPPORTS AND METHODS OF USING SAME

CROSS-REFERENCE TO RELATED APPLICATIONS

This application claims the benefit of U.S. Patent Ser. No. 63/110,635, filed Nov. 6, 2020, the entirety of which is hereby incorporated by reference.

FIELD

Embodiments of the present invention relate to systems for collecting urine specimens and methods of using such systems.

BACKGROUND

Urine analysis is required in a variety of situations and settings, such as during doctor's visits or as a term of employment (e.g., random drug testing). Regardless of the reason or the setting, providing a urine sample can be a messy process, particularly for women. For woman, providing a urine sample typically requires the user to suspend a specimen cup within the toilet at the location they believe the urine flow will be directed. Rarely is that location accurate. Rather, more often than not women end up urinating on their hand(s) as they scramble to adjust the location of the cup.

Specimen cup holders have been developed that effectively remove the hand from the situation. More specifically, the holders include a handle and a cup holder provided on a distal end of the handle. An aperture is provided within the cup holder for receiving a specimen cup. In use, the cup is positioned within the aperture and the user suspends the cup within the toilet using the handle. However, such prior holders have overwhelmingly been made of a non-absorbent material, such as plastic. Thus, if urine impacts the holder, it drips from the holder. Moreover, the design of these prior holders does not render them suitable for widespread dispensing and use in a restroom setting. More specifically, the geometry of prior holders makes it difficult (if not impossible) to provide multiple holders in a compact fashion. Overall, there is a need for an improved urine collection system that results in a more sanitary urine collection process.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Some embodiments are directed to a cup support having a top and a bottom. The cup support also includes a head portion defining an aperture having an aperture opening adapted to receive a specimen cup for the collection of a liquid, the aperture opening including a continuously curved, circular profile and a diameter configured to receive the specimen cup in a direction from the top to the bottom of the cup support. The cup support also includes a handle portion extending from the head portion. The head portion and the handle portion can be integrally formed, and the cup support is adapted to absorb liquid that impinges on it during use.

Other embodiments include a cup support having a top and a bottom and a head portion that includes a base wall having an outer perimeter and an inner wall that extends upwardly from the base wall in a direction away from the bottom of the cup support. The inner wall at least partially defines, and extends at least partially around, an aperture including an aperture opening adapted to receive a specimen cup for the collection of a liquid, the aperture opening including a continuously curved, circular profile and a diameter configured to receive the specimen cup in a direction from the top to the bottom of the cup support. The cup support also includes a handle portion extending from the head portion and including a base wall having an outer perimeter. An outer wall extends upwardly from, and around at least a portion of the outer perimeter of, at least one of the base wall of the head portion or the base wall of the handle portion in a direction away from the bottom of the cup support. In some embodiments, the head portion and the handle portion are integrally formed from a liquid absorbent material. A trough having a base may be defined between the outer wall and the inner wall on the head portion such that the base of the trough is located more proximate the bottom of the cup support than the aperture opening.

Other embodiments are directed to a stack of nested cup supports. Each cup support includes a head in which is defined an aperture having a diameter configured to receive, in a direction from the top to the bottom of the cup support, a specimen cup for the collection of a liquid, where the head includes an outer wall that extends around at least a portion of a perimeter of the head and upwardly in a direction away from the bottom of the cup support. The cup supports also include a handle extending from, and integrally formed with, the head. When nested, the head of an upper cup support in the stack of cup supports is at least partially received within the outer wall of the head of a cup support located immediately below the upper cup support in the stack of cup supports.

BRIEF DESCRIPTION OF THE FIGURES

Illustrative embodiments of the present invention are described in detail below with reference to the following photographs.

DETAILED DESCRIPTION

Figure 1:
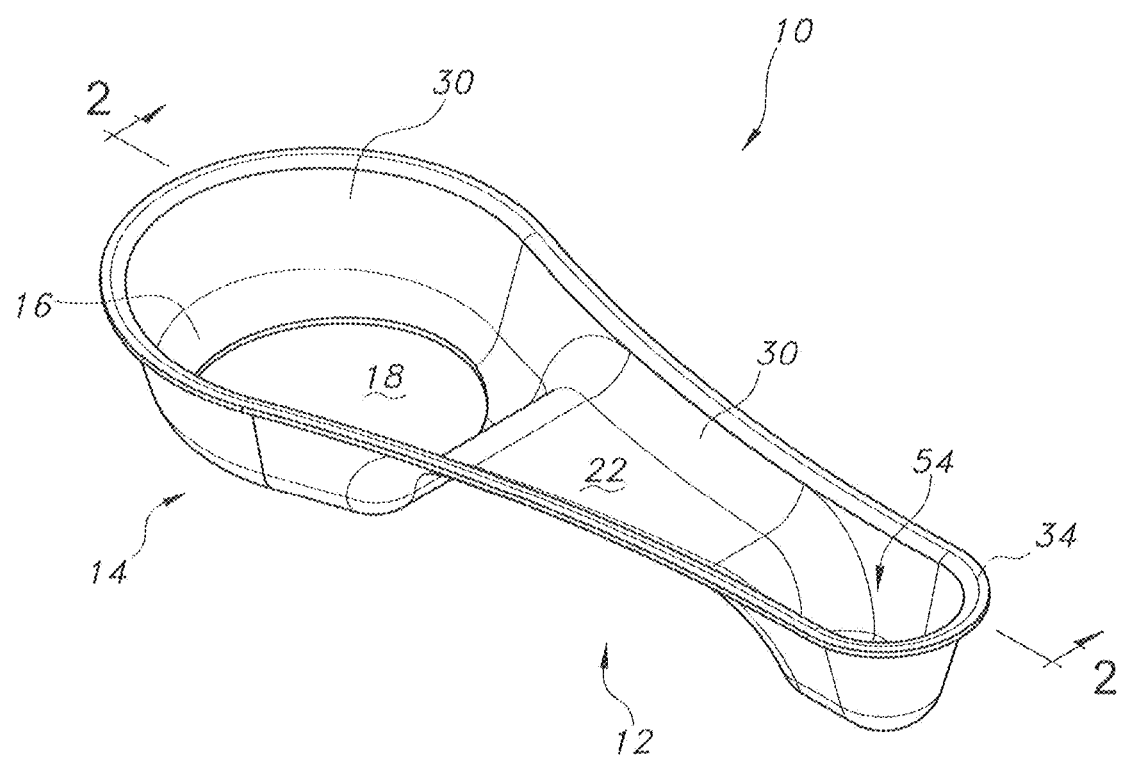
FIG. 1 is a top perspective view of an embodiment of a cup support.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments of the present invention include a specimen collection system that includes a cup support having a handle and head extending from one end of the handle. An aperture is provided within the head for receiving a specimen cup. In use, the specimen cup is positioned within the aperture so as to be supported by the head of the cup support, and the user suspends the cup within the toilet using the handle. In this way, the user's hand is remote from the situation and thus less likely to get soiled during use. Note that while this disclosure describes the invention with respect to urine collection, it is not so limited. Rather, it may be applied to other circumstances where collection of a liquid is desired. Moreover, it should be noted that the users of the cup supports disclosed herein may be the person providing the sample, but may also be a third party overseeing the urine sample collection process.

In some embodiments, all of the features of the cup support disclosed herein are formed integrally of a single material. It is preferable, but not required, that the cup support be formed from recycled and/or renewable materials. In some embodiments, the cup support is formed from one or more biodegradable materials. The cup support can be formed of any material, such as, but not limited to, cellulose materials, polymeric materials, ceramics, metallic materials (e.g., stainless steel, etc.), and silicon/silicone materials. While embodiments of the cup support may be designed for multiple uses (e.g., used once and sterilized for subsequent use), in some embodiments the cup support is formed of a material designed for a single use, such as cellulose (e.g., pulp/paper) or thin plastic. In some embodiments, the cup support is adapted to absorb liquid that impinges upon the cup support. For example, in some embodiments the cup support is formed of a material that is naturally absorbent to liquids or that has been adapted to be absorbent to liquids, such as cellulose fibers and more specifically pulp fibers. This is in contrast to prior designs which have primarily been formed of naturally non-absorbent materials or materials that have been rendered non-absorbent (e.g., coated with a water/liquid resistant material). If urine impacts such non-absorbent holders, it is apt to drip from the cup support.

In other embodiments, the handle and the head may be formed separately (of the same or different materials) and subsequently attached or connected to each other for use. For example, the handle could be formed of a material that permits its reuse, while the head could be formed of a material designed for single use.

The cup support can be formed via any of a variety of methods, including, but not limited to, compression molding, transfer molding, injection molding, thermo-forming, vacuum-forming, etc.

FIGS. 1, 2, and 8-14 illustrate a cup support 10 in accordance with one embodiment of the present invention. The cup support 10 includes a handle portion 12 and a head portion 14. The head portion 14 includes a head base wall 16 in which is defined an aperture 18. Given that most specimen cups are circular, in some embodiments the aperture 18 is substantially circular. In some embodiments, the aperture 18 has a continuous smooth circular shape devoid of inwardly projecting tabs or other retention features. In this way, a cup can be dropped into the aperture 18 and in substantially 360° degree contact with the edge of the cup support 10 defining the aperture 18 (i.e., there is a substantially gap-free interface or joint between the cup and the cup support 10). However, in other embodiments inwardly projecting tabs or other retention features are provided on the aperture 18.

Any diameter of aperture 18 may be provided, but the diameter of the aperture 18 is preferably selected such that a variety of different-sized specimen cups may be dropped into and retained within the aperture 18 without falling through the aperture 18. For example, larger diameter cups would simply not extend as far within the aperture 18 as smaller-diameter cups. In this way, the cup support 10 can be used universally with a variety of different specimen cups. Aperture diameters of between one and six inches, inclusive; between one and five inches, inclusive; between one and four inches, inclusive; between one and three inches inclusive; between one and two inches inclusive; between two and five inches inclusive; between two and four inches, inclusive; between two and three inches, inclusive; between three and six inches, inclusive; between three and five inches, inclusive; and between three and four inches, inclusive will typically be suitable for most specimen cups.

In some embodiments, the base wall 16 is planar and/or extends radially outwardly from the aperture so as to extend co-planar with the aperture 18 (i.e., approximately 90° relative to the aperture axis y). However, in other embodiments, the base wall 16 can angle upwardly or downwardly from the aperture 18, such as at a non-zero angle that is greater than 0° but less than 90° when measured upwardly or downwardly from the aperture axis y (e.g., extending at an angle equal to or greater than 5°, 10°, 15°, 20°, 25°, 30°, 35°, 40°, 45°, 50°, 55°, 60°, 65°, 70°, 75°, 80°, or 85° but less than 90° when measured upwardly or downwardly from the aperture axis y).

The handle portion 12 can be of any length L but is preferably of a length that sufficiently distances the hand of the user from the urine stream during use. In some embodiments, the handle portion 14 has a length L between one and ten inches, inclusive; between one and eight inches, inclusive; between one and six inches, inclusive; between two and five inches, inclusive; between two and four inches, inclusive; between one and four inches, inclusive; between one and three inches, inclusive; between two and three inches, inclusive; between three and six inches, inclusive; or between three and five inches, inclusive. In some embodiments, the handle length L will be at least 1 inch, at least 1.5 inches, at least 2 inches, at least 3 inches, or at least 4 inches, but less than 10 inches, less than 8 inches, less than 7 inches, less than 6 inches, or less than 5 inches.

The handle portion 12 includes a handle base wall 22. The handle base wall 22 can laterally curve upwardly or downwardly across the handle portion 12 (in a direction perpendicular to the axis x of the handle portion 12). In other embodiments, the handle base wall 22 extends substantially in a plane. In some embodiments, the handle base wall 22 and the head base wall 16 extend coplanar (see FIGS. 5 and 6). However, in other embodiments, the handle base wall 22 and the head base wall 16 extend in different planes. For example, the plane of the handle base wall 22 may be angled relative to the plane of the head base wall 16 such that the handle portion 12 extends upwardly relative to the head portion 14. However, in other embodiments, the plane of the handle base wall 22 and the plane of the head base wall 16 extend substantially (or exactly) parallel but offset from each other (see FIGS. 1-4). For example, in some embodiments, the plane of the handle base wall 22 extends substantially parallel but above the plane of the head base wall 16. By "above" it is meant that the plane of the handle portion 12 is more proximate the user than the plane of the head portion 14 during use. In such embodiments, the handle base wall 22 and the head base wall 16 are connected by a transition wall 24 that extends between the handle base wall 22 and the head base wall 16. In some embodiments, the transition wall 24 is curved while in other embodiments the transition wall 24 is straight and angled relative to the planes of the handle base wall 22 and head base wall 16. In some embodiments, the transition wall 24 extends substantially perpendicular to the plane of the head portion 14 and/or the plane of the handle portion 12, but in other embodiments the angle is less severe (i.e., the plane of the transition wall 24 is greater than 0° but less than 90° relative to the plane of the head portion 14 and/or handle portion 12).

An outer upstanding portion or wall 30 may be, but does not have to be, provided around a portion or all of the outer perimeter of the cup support 10. More specifically, an outer upstanding wall 30 may extend upwardly from one or both of the head base wall 16 or handle base wall 22. By "upwardly" it is meant that the wall extends in a direction that would be towards the user during use. The outer upstanding wall 30 may be continuous around the perimeter of the cup support 10 or multiple wall segments may be used. The outer upstanding wall 30 may extend directly upwardly from one or both of the head base wall 16 and/or handle base wall 22 (e.g., at approximately 90° relative to the plane of the head base wall 16 or handle base wall 22) or may angle inwardly or outwardly relative to the head portion 14 and/or handle portion 12. In some embodiments, the outer upstanding wall 30 angles outwardly at an angle B measured downwardly from the aperture axis y, such as but not limited to at an angle B (i) greater than 5°, greater than 10°, greater than 15°, greater than 20°, greater than 25°, greater than 30°, greater than 35°, greater than 40°, greater than 45°, greater than 50°, greater than 55°, greater than 60°, greater than 65°, greater than 70°, greater than 75°, greater than 80°, or greater than 85, but (ii) less than 90°. The outer upstanding wall 30 serves to impart structural rigidity to the cup support 10 and render the cup support 10 better able to support the weight of a filled specimen cup. Moreover, it also helps to contain errant urine streams on the cup support 10 to prevent any dripping from the edges of the cup support 10, as described below. However, not all embodiments of the cup supports described herein will include an outer upstanding wall 30. Moreover, such an outer upstanding wall 30 need not be provided around the entire perimeter of the cup support. Rather, in some embodiments, it may be provided around all or a portion of the perimeter of the head portion 14 but not along the perimeter of the handle portion 12 (or vice versa).

The height H of the outer upstanding wall 30 (which can be measured from the head base wall 16 or handle base wall 22) can be consistent or vary along the perimeter of the cup support 10. In some embodiments, the upstanding wall has a height H of at least 1 millimeter ("mm"), at least 2 mm, at least 3 mm, at least 4 mm, at least 5 mm, at least 6 mm, at least 7 mm, at least 8 mm, at least 9 mm or at least 10 mm, but less than 80 mm, less than 70 mm, less than 60 mm, less than 50 mm, less than 40 mm, less than 30 mm, less than 20 mm, or less than 10 mm. A height H between 2 mm to 30 mm, inclusive; 2 mm to 25 mm, inclusive; 2 mm to 20 mm, inclusive; 2 mm to 15 mm, inclusive; 2 mm to 10 mm, inclusive; 2 mm to 8 mm inclusive; 2 mm to 5 mm inclusive; or 5 mm to 10 mm, inclusive, will be suitable for most applications. The height H of the outer upstanding wall 30 may be consistent or vary around the perimeter of the cup support 10. In some embodiments, the distal edge(s) of the outer upstanding wall 30 terminate in a single plane. By way only of example, in embodiments where the handle portion 12 extends in a plane above the head portion 14, the height H of the upstanding wall portion(s) 30 extending along the perimeter of the head portion 14 may be greater than the height H of the upstanding wall portion(s) 30 extending along the perimeter of the handle portion 12 such that the outer upstanding wall 30 terminates in the same plane.

In some embodiments, a rim 34 extends outwardly from the distal end of the entire, or portions of, the outer upstanding wall 30. Such a rim 34 further imparts structural rigidity to the cup support 10 but also facilitates removal of a cup support 10 from a stack of nested cup supports, as discussed in further detail below.

Figure 2:
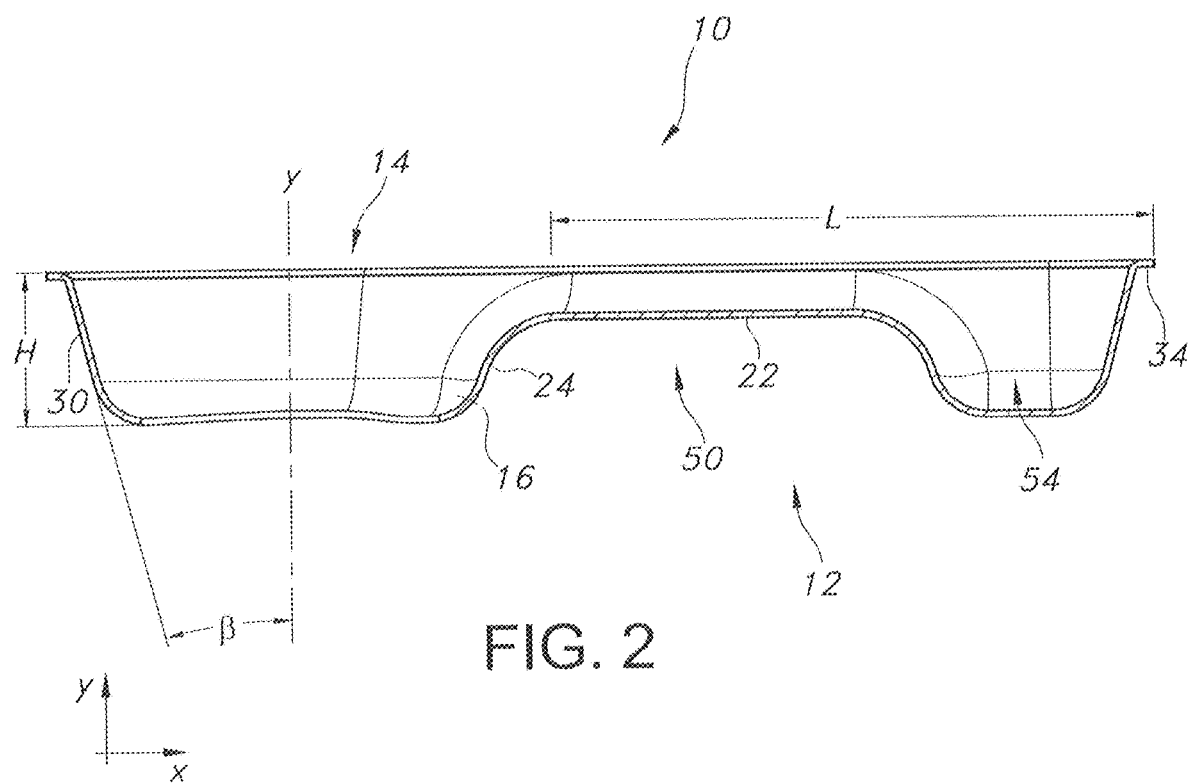
FIG. 2 is a cross-sectional view taken along line 2-2 in FIG. 1.
Figure 3:
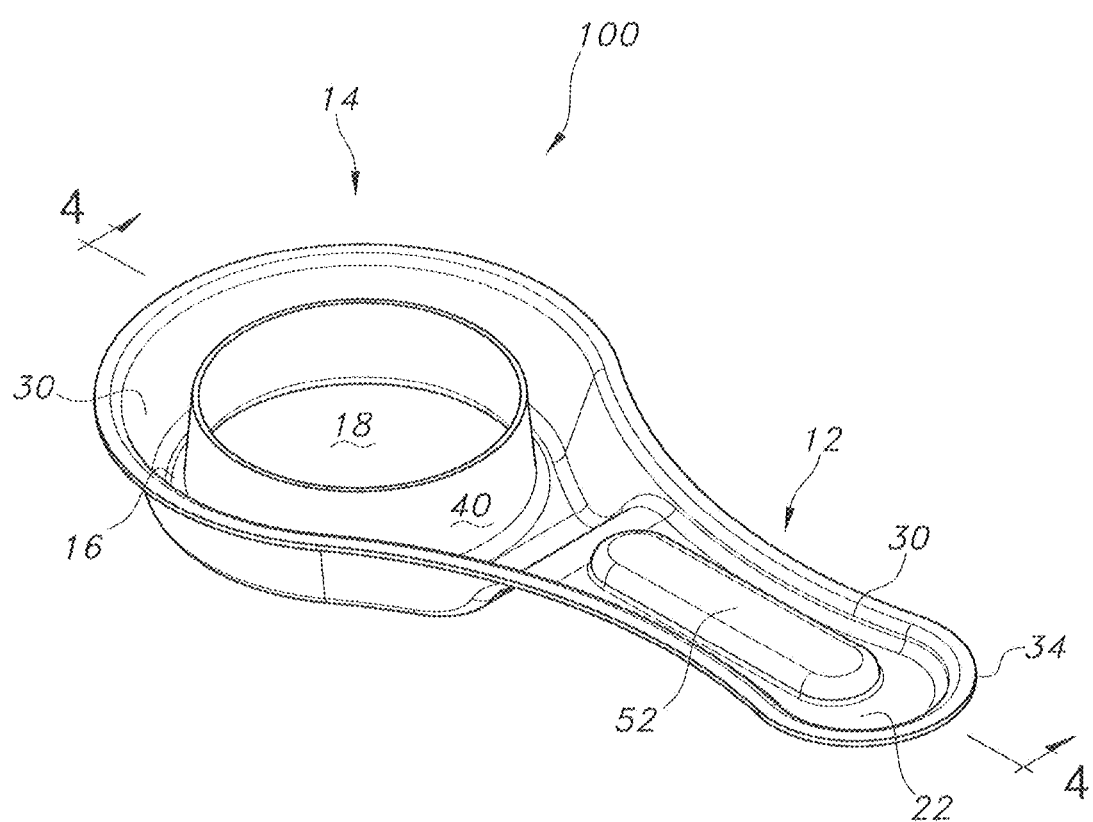
FIG. 3 is a top perspective view of another embodiment of a cup support.
Figure 4:
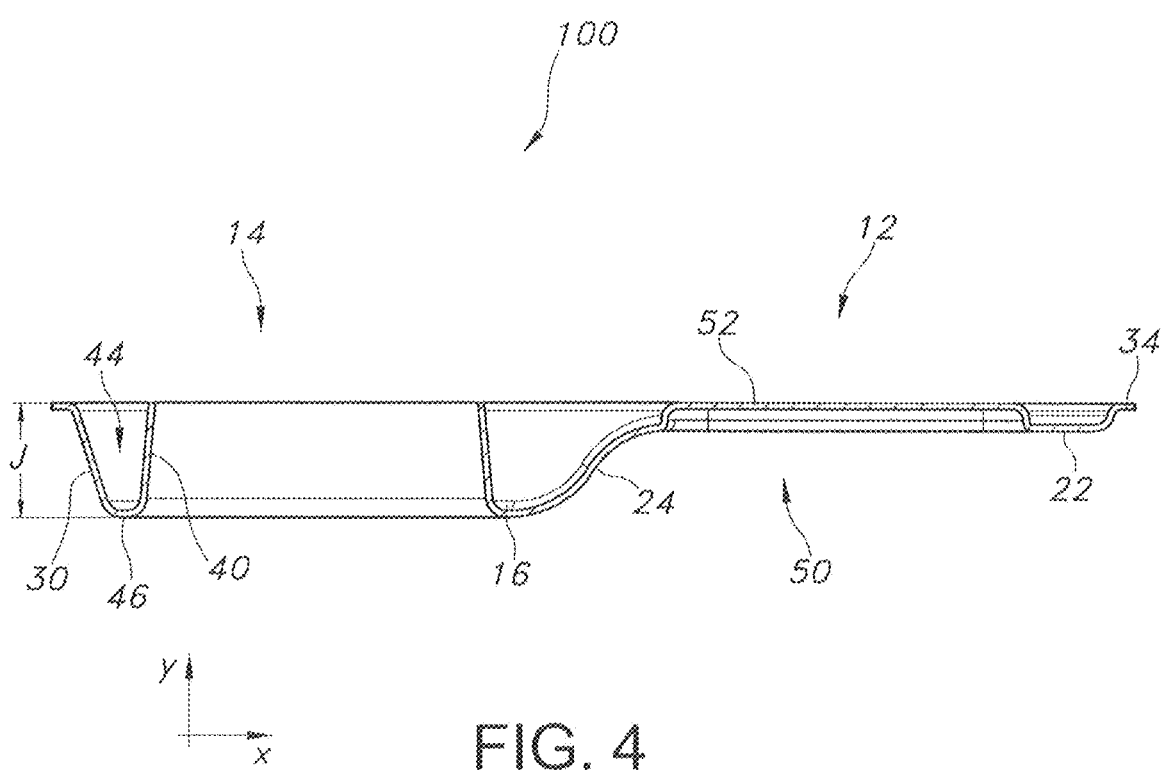
FIG. 4 is a cross-sectional view taken along line 4-4 in FIG. 3.

FIGS. 3, 4, and 15-21 and FIGS. 5, 6, and 22-28 illustrate alternative embodiments of a cup support 100, 200 that are similar to the cup support 10 of FIGS. 1 and 2 such that like reference numbers are used to denote identical features. However, cup supports 100, 200 include an inner upwardly curved and/or upstanding portion or wall 40 that extends at least partially around the perimeter of the aperture 18. The inner upstanding wall 40 can partially or entirely encircle the aperture 18. In some embodiments, the inner upstanding wall 40 is in the form of a cylinder or truncated cone. The inner upstanding wall 40 can extend upwardly substantially parallel to aperture axis y or at a non-parallel angle relative to the aperture axis y (inwardly or outwardly relative to the aperture 18). The inner upstanding wall 40 extends to a height J that can be greater than, less than or equal to the height H of the outer upstanding wall 30. In some embodiments, the distal edge of the inner upstanding wall 40 is recessed below or co-terminates with the distal edge of the outer upstanding wall 30 extending along the head portion 14 of the cup support 100. However, in other embodiments the distal edge of the inner upstanding wall 40 extends above the distal edge of the outer upstanding wall 30.

Figure 5:
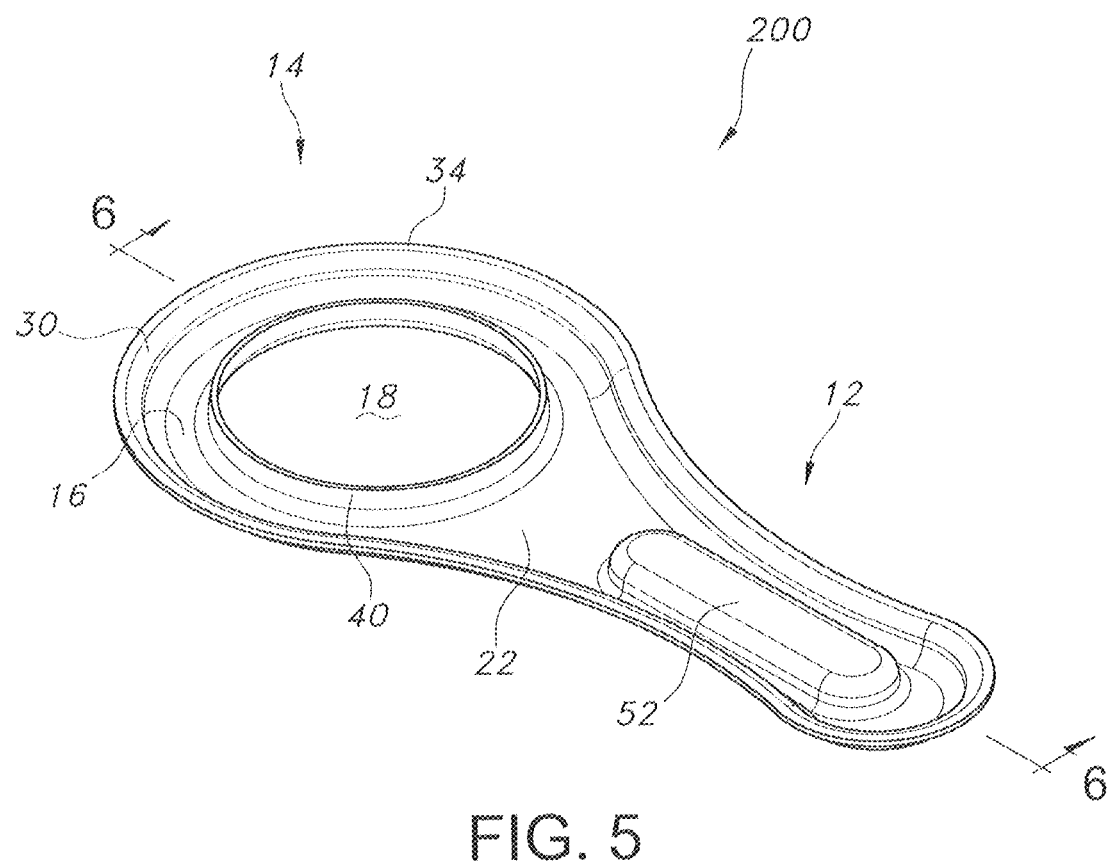
FIG. 5 is a top perspective view of still another embodiment of a cup support.
Figure 6:
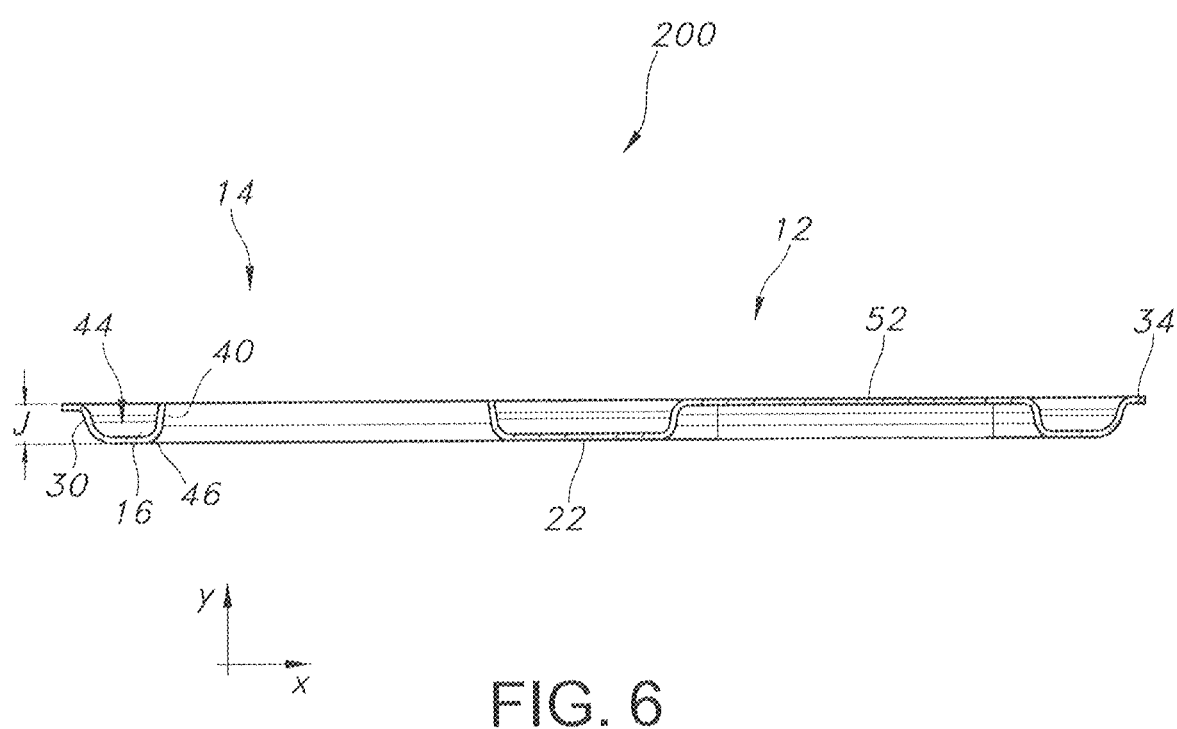
FIG. 6 is a cross-sectional view taken along line 6-6 in FIG. 5.

In some embodiments, the outer upstanding wall 30 is formed by the perimeter edge of the head base wall 16 curving, bending, and/or flaring upwardly, inwardly, and/or outwardly to define the outer upstanding wall 30 (see, e.g., FIGS. 5, 6). In some embodiments, the inner upstanding wall 40 is formed by the edge of the head base wall 16 that defines the aperture 18 curving, bending, and/or flaring upwardly, inwardly, and/or outwardly to define the inner upstanding wall 40 (see, e.g., FIGS. 5, 6).

In some embodiments, the head portion 14 does not include a head base wall 16. Rather, the aperture 18 can be defined directly by the outer upstanding wall 30 or the inner upstanding wall 40. For example, the head portion 14 may include an outer upstanding wall 30 that extends downwardly, and the aperture 18 is defined by the lower edge of the outer upstanding wall 30. Or, alternatively, the upper edge of the inner upstanding wall 40 may define the upper aperture opening. In some embodiments, the outer upstanding wall 30 and inner upstanding wall 40 meet at a V-shaped intersection such that no head base wall 16 is present. In some embodiments, the inner upstanding wall 40 and the outer upstanding wall 30 (along with the head base wall 16 if provided) form a trough 44 that extends at least partially around the perimeter of the aperture 18. In some embodiments, the base 46 of the trough 44 is recessed below the upper aperture opening that receives the specimen cup. As described further below, in use the inner upstanding wall 40 directs errant urine away from the joint between the cup support 100, 200 and the specimen cup and into the trough 44.

In some embodiments, the cup supports are designed such that they can be nested within each other to permit stacking. More specifically, in some embodiments, at least part of the head portion 14 and/or handle portion 12 of a cup support located higher in the stack seats at least partially within the head portion 14 and/or handle portion 12 of the cup support located immediately below it in the stack. For example, in some embodiments, the head portion 14 and/or handle portion 12 of an upper cup support seats within the outer upstanding wall 30 of a lower cup support. Slightly outwardly flared or angled outer upstanding walls 30 can assist with such stacking, although they are not required. In embodiments provided with inner upstanding walls 40, the inner upstanding wall 40 of the cup support located lower in the stack can be at least partially received within the aperture of the cup support located immediately higher in the stack.

Figure 7:
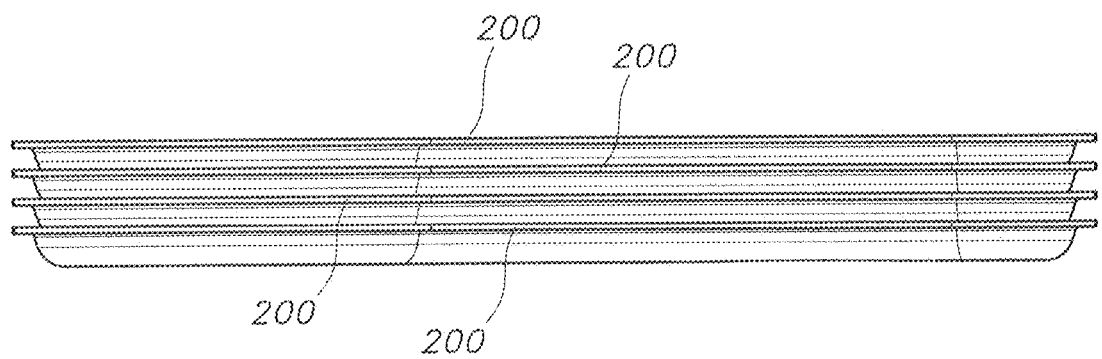
FIG. 7 is a side elevation view of a stack of the cup supports of FIG. 5.
Figure 8:
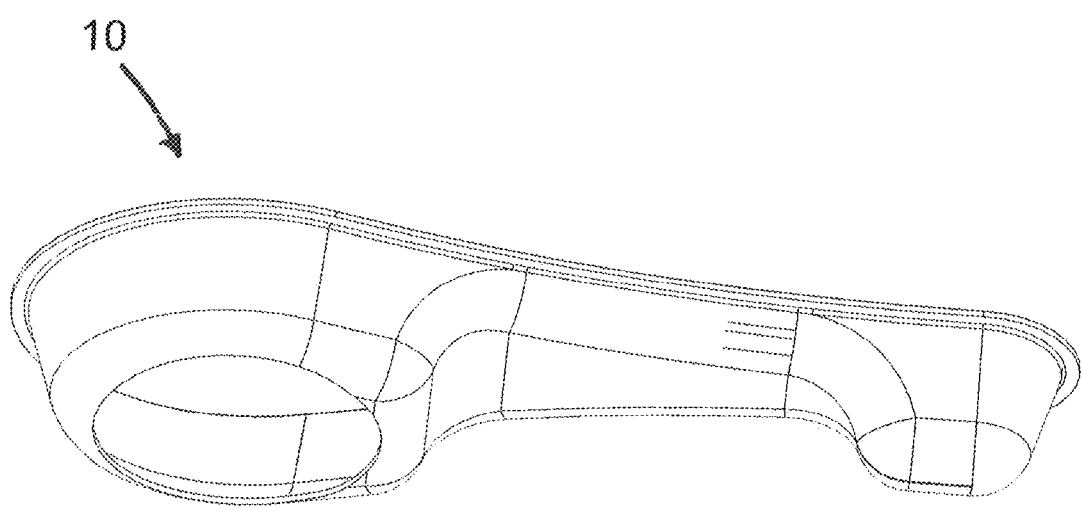
FIG. 8 is bottom perspective view of the cup support of FIG. 1.
Figure 9:
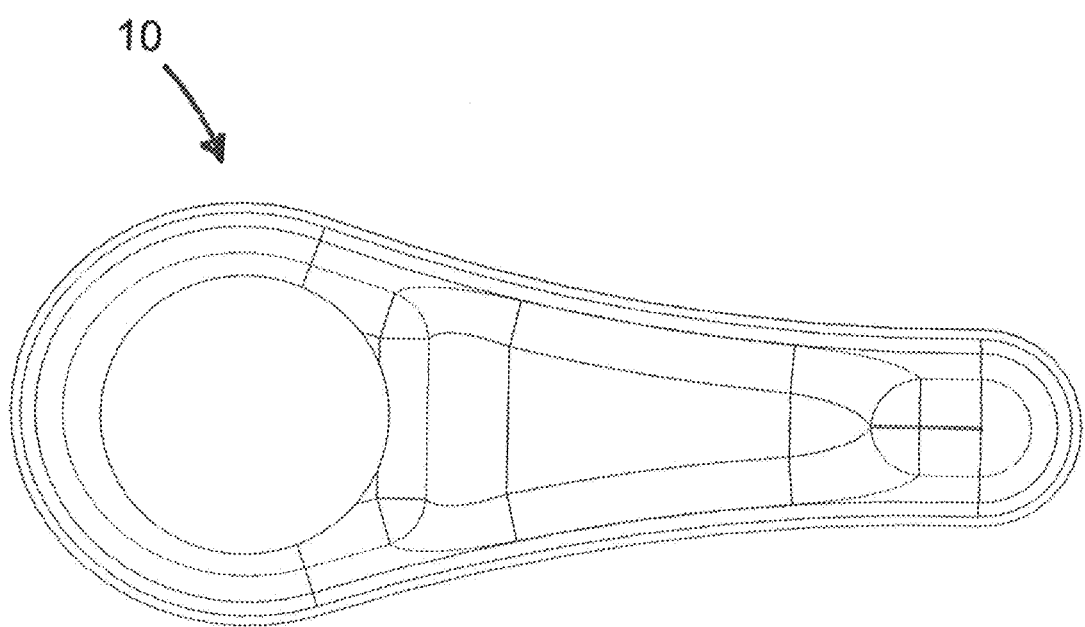
FIG. 9 is a top plan view of the cup support of FIG. 1.
Figure 10:
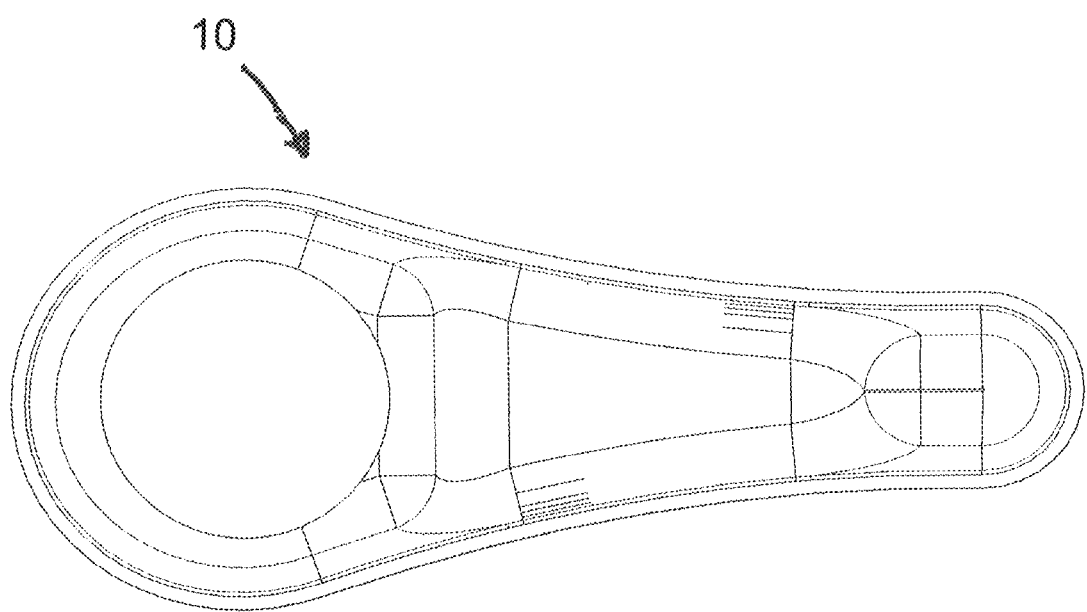
FIG. 10 is a bottom plan view of the cup support of FIG. 1.
Figure 11:
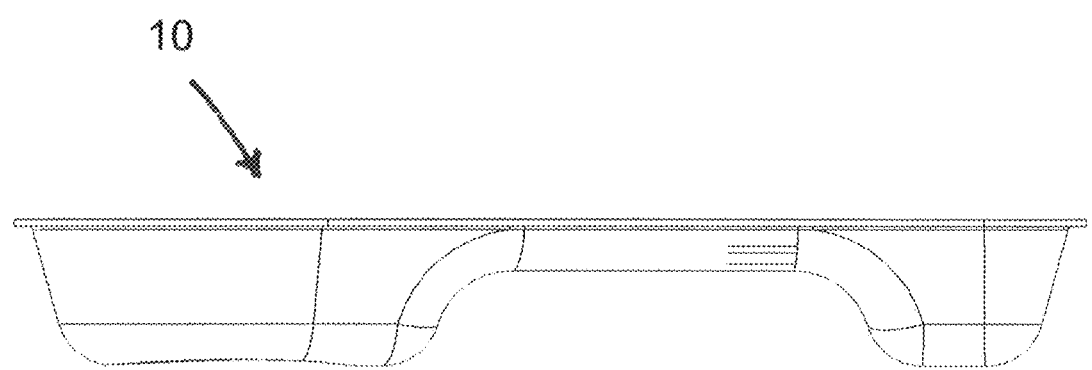
FIG. 11 is a front side elevation view of the cup support of FIG. 1.
Figure 12:
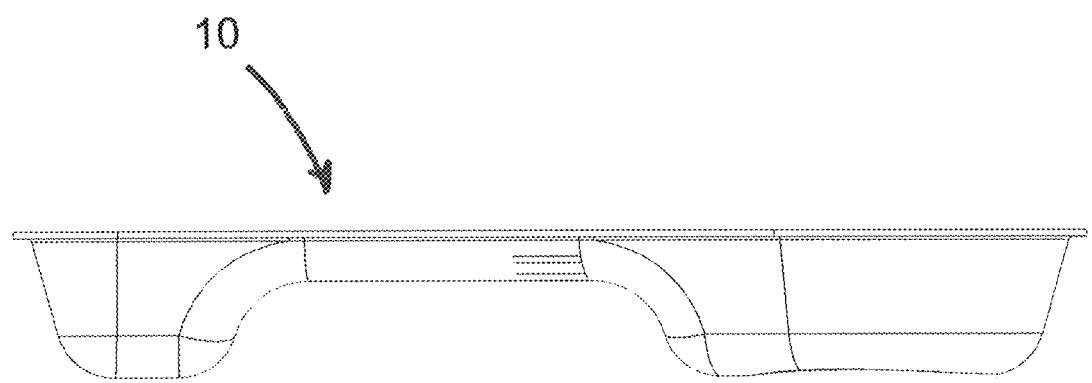
FIG. 12 is a rear side elevation view of the cup support of FIG. 1.
Figure 13:
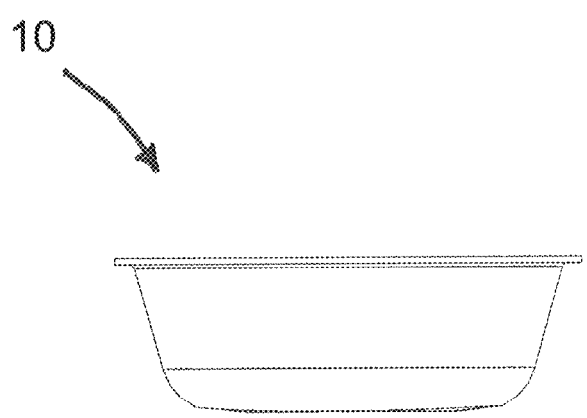
FIG. 13 is a left end view of the cup support of FIG. 1.
Figure 14:
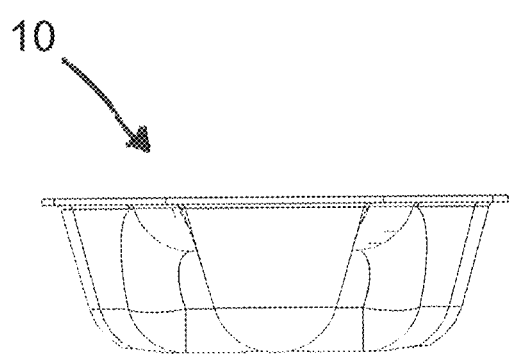
FIG. 14 is a right end view of the cup support of FIG. 1.
Figure 15:
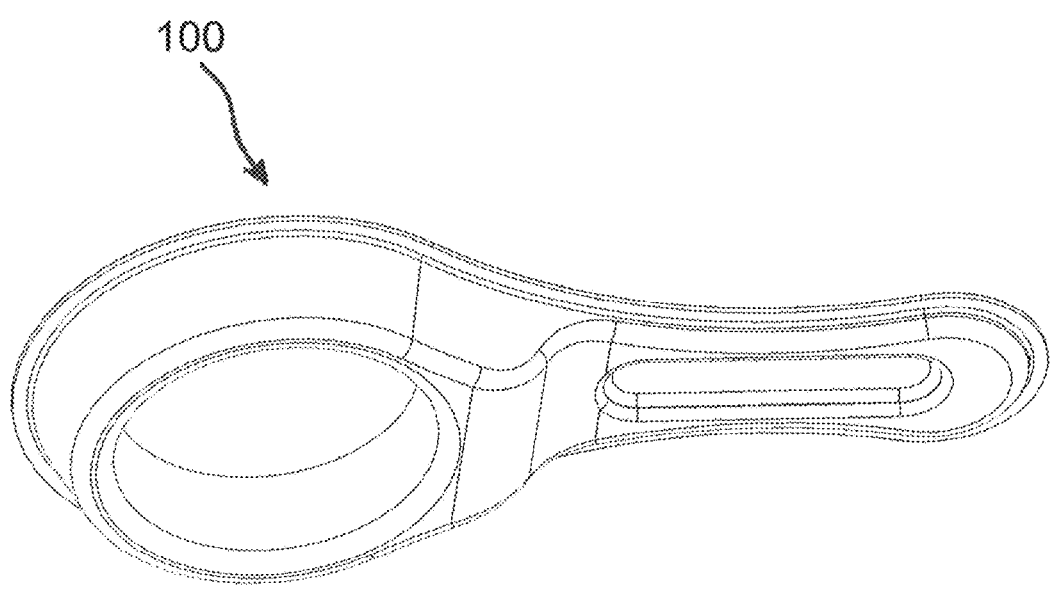
FIG. 15 is a bottom perspective view of the cup support of FIG. 3.
Figure 16:
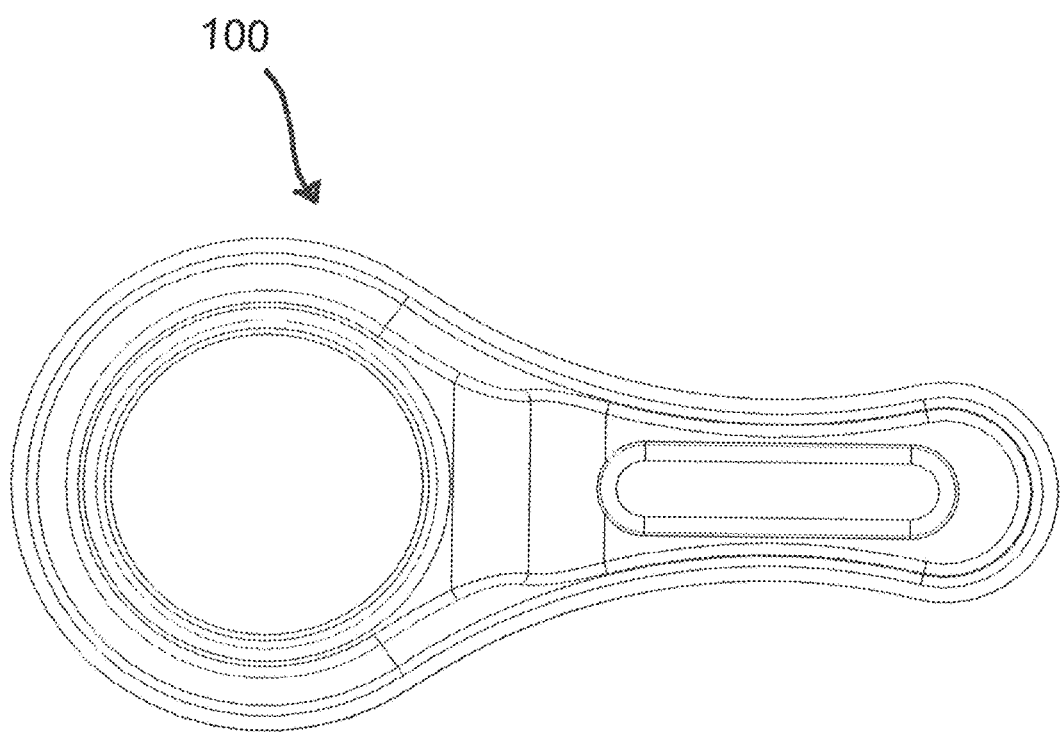
FIG. 16 is a top plan view of the cup support of FIG. 3.
Figure 17:
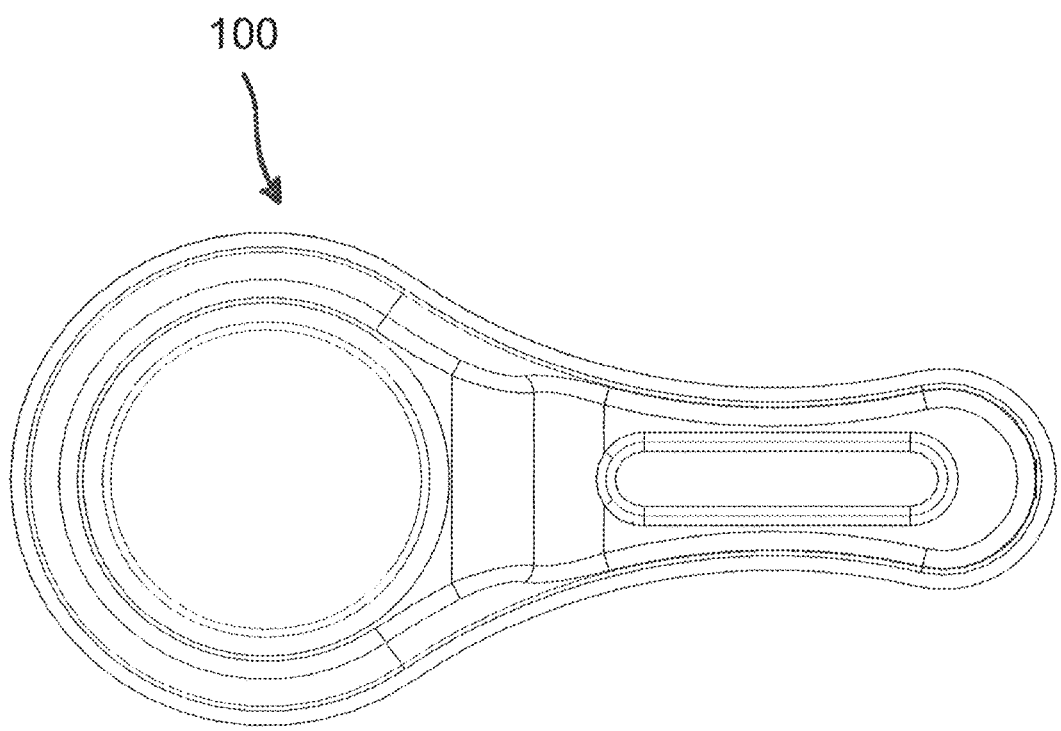
FIG. 17 is a bottom plan view of the cup support of FIG. 3.
Figure 18:
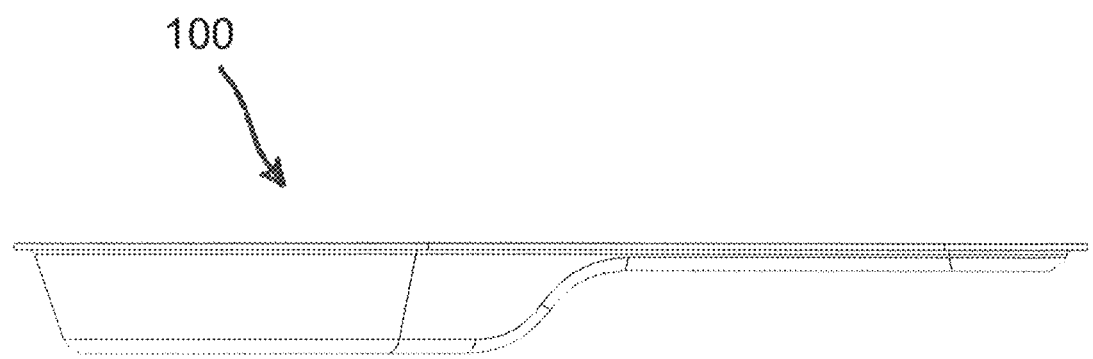
FIG. 18 is a front side elevation view of the cup support of FIG. 3.
Figure 19:
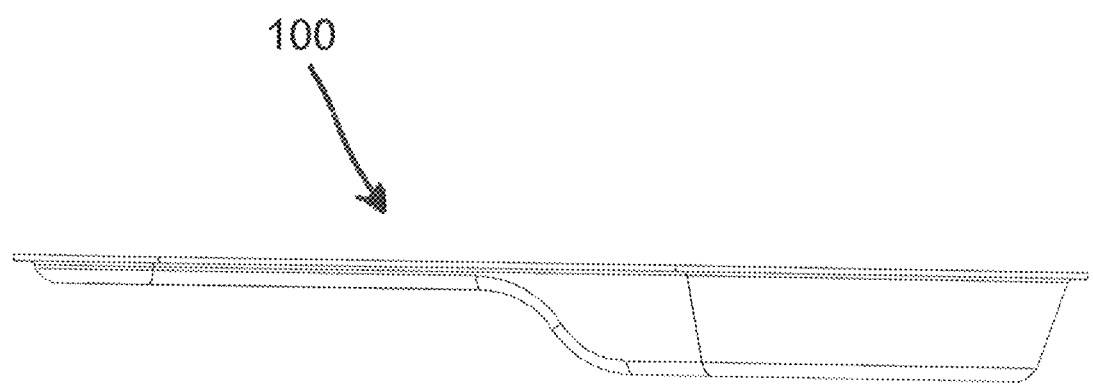
FIG. 19 is a rear side elevation view of the cup support of FIG. 3.
Figure 20:
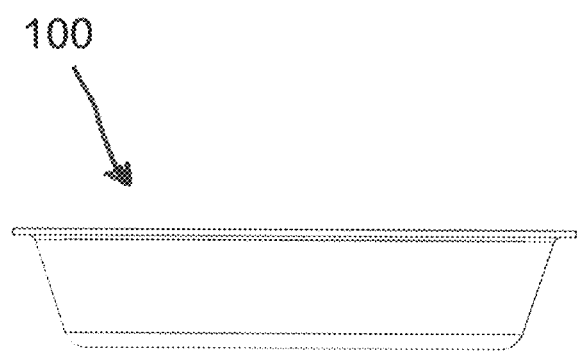
FIG. 20 is a left end view of the cup support of FIG. 3.
Figure 21:
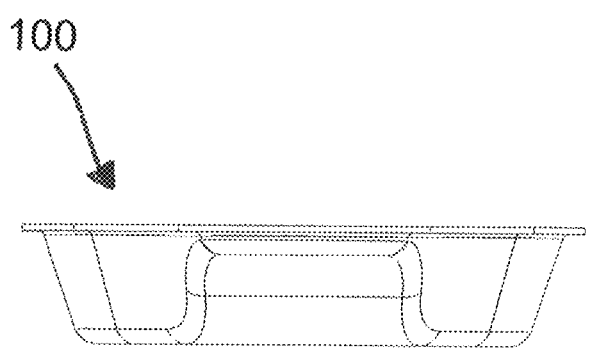
FIG. 21 is a right end view of the cup support of FIG. 3.
Figure 22:
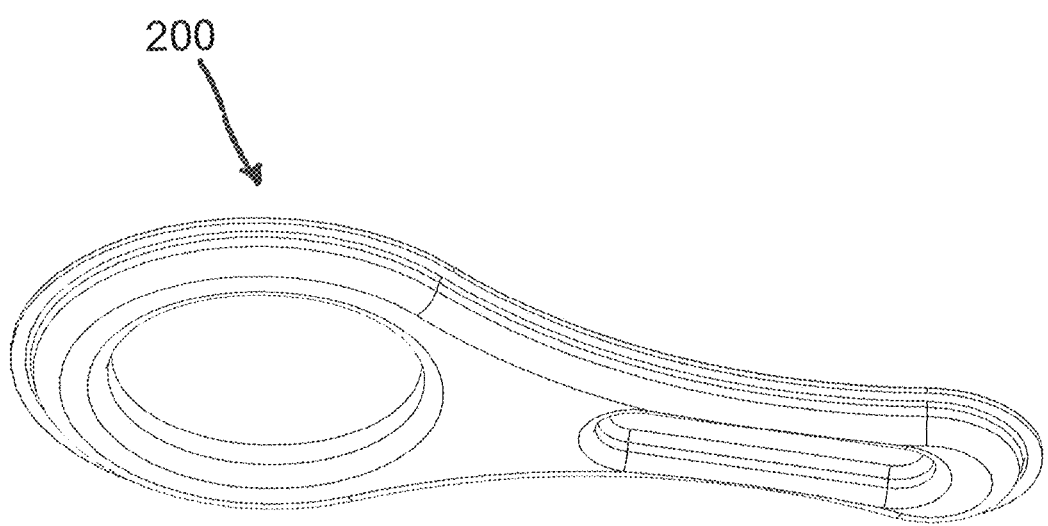
FIG. 22 is a bottom perspective view of the cup support of FIG. 5.
Figure 23:
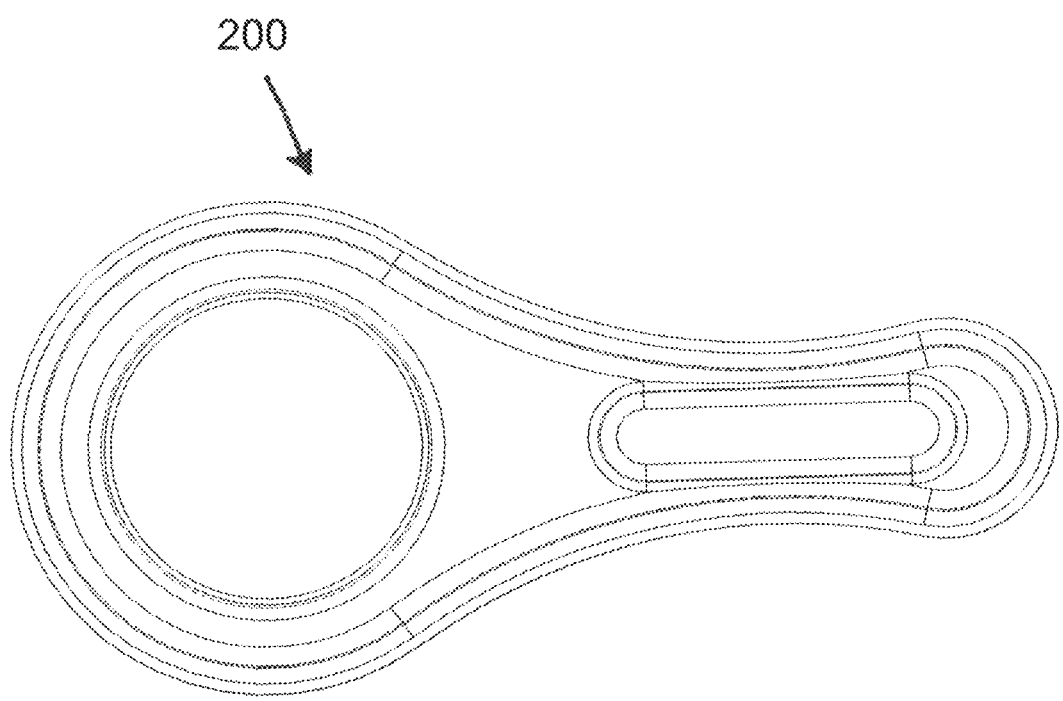
FIG. 23 is a top plan view of the cup support of FIG. 5.
Figure 24:
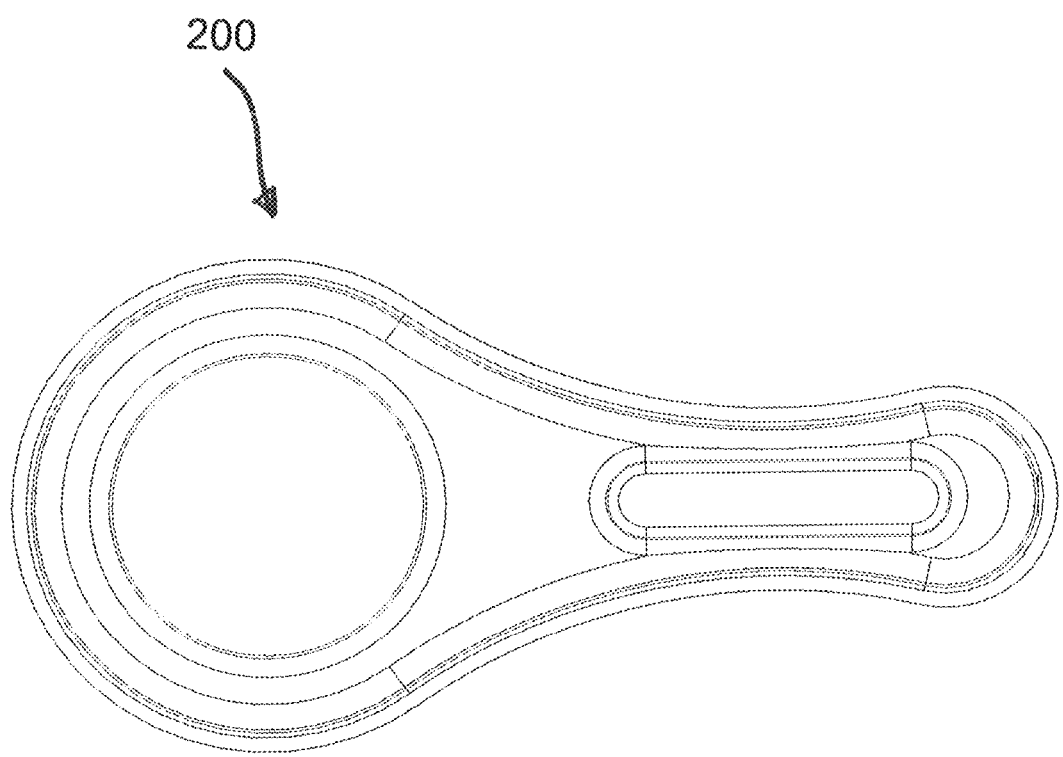
FIG. 24 is a bottom plan view of the cup support of FIG. 5.
Figure 25:
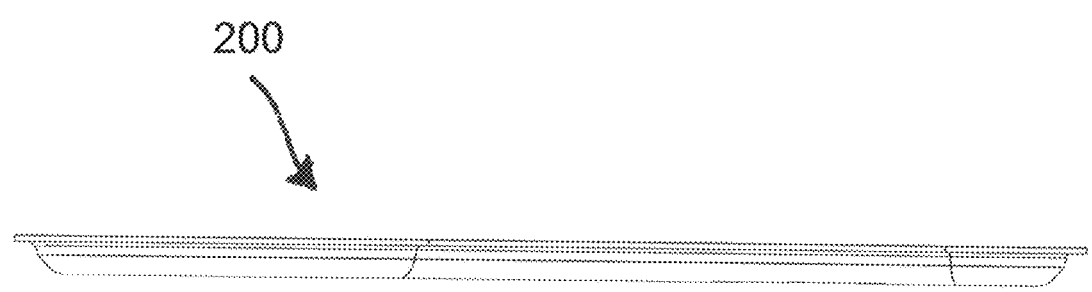
FIG. 25 is a front side elevation view of the cup support of FIG. 5.
Figure 26:
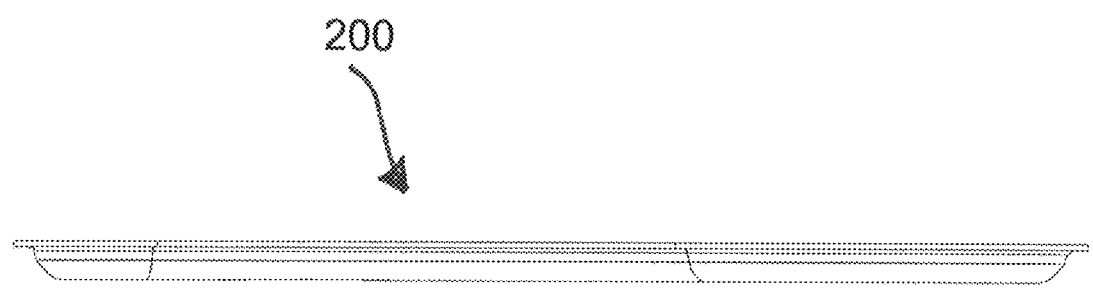
FIG. 26 is a rear side elevation view of the cup support of FIG. 5.
Figure 27:
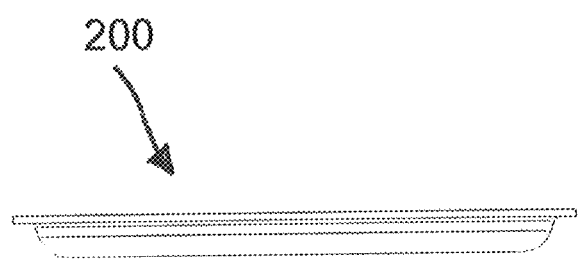
FIG. 27 is a left end view of the cup support of FIG. 5.
Figure 28:
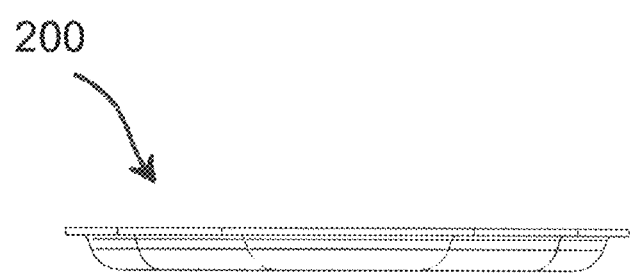
FIG. 28 is a right end view of the cup support of FIG. 5.

In some embodiments, the cup support is shaped such that the contour of the lower portion of the cup support forms an undercut 50 (see FIGS. 1-4) that receives a portion of the handle of the cup support located immediately below it in the stack. In some embodiments, features are provided on the handle such that a portion of an upper or lower handle in the stack is received within a portion of a lower or upper handle, respectively. This ability to nest adjacent cup supports with each other enables a compact stack of cup supports to be provided to seat on a counter or back of a toilet within a restroom. An example of a nested/stacked cup support arrangement is shown in FIG. 7. Moreover, nesting or engagement between adjacent cup supports laterally interlocks the cup supports together so as to prevent relative sliding between them (which can result in them falling onto the bathroom floor). It should be noted, however, that the cup supports described herein need not be stacked but rather may be provided individually to the user. In some embodiments, the cup supports are individually wrapped.

If the cup supports are provided in a stack, in use the user lifts the cup support from the top of the stack. Rim 34 (if provided) may facilitate this process. The user then drops a specimen cup into the aperture. A single size aperture may accommodate specimen cups of varying diameters. In embodiments where the aperture 18 is smooth and continuous, cups are free to drop through the aperture to a point at which the outer diameter of the cup abuts the edge defining the aperture. This point will be different for cups of different diameters. Regardless, at that point the cup is fully encircled by the cup support such that substantially no gap exists between the cup and cup support. This helps to prevent liquid from seeping down through the joint between the cup and the cup support. Embodiments where tabs or retentions features are provided in the aperture may require the user to apply light pressure to insert the cup within the aperture.

Gripping the handle (typically between the user's thumb and forefinger), the user then positions the cup (supported by the head portion 14) in the anticipated location of the urine stream. The user can re-adjust positioning using the handle and based on the direction of the initial urine flow. One or more ribs 52 (see FIGS. 3-6), divots 54 (see FIGS. 1-2), apertures, surface texturing, or other features may optionally be provided on the handle to enhance the rigidity of the handle and/or facilitate gripping of the handle by the user.

If the user initially fails to position the cup opening directly in the "line of fire" of the urine stream, the outer upstanding wall 30 prevents errant urine from dripping off the sides of the cup support. In the embodiment of FIGS. 3-6, errant liquid is directed by the inner upstanding wall 40 into the trough 44. Moreover, the transition wall 24 and/or ribs 52 (if present) serve as a back stop and/or obstacle to prevent the liquid from reaching the user's hand. For example, in the embodiments provided with one or more ribs 52, the user can grip the handle such that the thumb or other finger rests on top of the rib 52. To the extent urine travels along the cup support towards the handle during use (which may occur particularly if the cup support is not made from a liquid absorbent material), the rib 52 elevates the user's thumb or finger out of the path of the urine. Instead, the urine is directed along a path around the rib 52.

In some embodiments, the cup support is adapted to absorb at least some of the liquid that impinges on it. For example, in some embodiments, the cup support is formed from a liquid absorbent material, such as compressed or molded cellulose fibers such as pulp fibers (e.g., raw pulp fibers), such as used to form some egg containers. The material should be of a suitable rigidity and thickness to bear the weight of a filled cup, even when the material gets wet during use. Suitable thicknesses of the material used to form the cup support include, but are not limited to, 1 millimeter to 10 millimeters, inclusive or 1 millimeter to 5 millimeters, inclusive. Thicknesses in the range of 1 millimeter to 4 millimeters will be suitable for most applications. If the cup is improperly aligned and urine impinges on a cup support formed of a liquid absorbent material, it will be absorbed by and into the cup support itself. Moreover, pulp fibers will be exposed in the exposed edges of the cup support, such as the edge defining the aperture 18 and/or the exposed edges of the inner or outer upstanding walls 40, 30 or rim 34. These exposed fibers are particularly effective at absorbing liquid.

During the urine collection process, not part of the cup support comes into contact with the urine that is deposited within the cup. Moreover, the design of embodiments of the present invention results in no urine reaching the user's hand or dripping from the cup or cup support after the specimen is deposited. Indeed, the bottom of the cup remains urine-free. Thus, upon completion, the user can set the cup support with associated cup down to redress without leaving urine of any surfaces. The user can then deposit both the cup support and the cup in the designated location for subsequent testing. It is contemplated that the handle portion may be scored, perforated, etc. such that it can be bent upwardly or downwardly to reduce the footprint of the assembly if necessary. In some embodiments, when the cup is set down, the cup support drops downwardly by virtue of gravity such that the cup and the cup support are automatically separated from each other. The nurse or other clinical personnel can then easily remove the cup for testing its contents and dispose of the cup support. In this way, the cup support is a hygienic, inexpensive, easy to use, single use product.

The foregoing is provided for purposes of illustrating, explaining, and describing embodiments of the present invention. Further modifications and adaptations to these embodiments will be apparent to those skilled in the art and may be made without departing from the scope or spirit of the invention. Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the invention.

We claim:

1. A cup support having an upper side and a lower side and comprising:
   a. a head portion comprising:
      i. a head base wall extending within a plane and having an outer perimeter; and
      ii. an inner upstanding wall extending from the head base wall towards the upper side of the cup support at an angle to the plane of the head base wall so as to extend non-coplanar and non-parallel with the head base wall, wherein the inner upstanding wall defines an aperture comprising an aperture opening configured to receive, in a direction from the upper side to the lower side of the cup support, a specimen cup for collection of a stream of liquid;
   b. a handle portion extending from the head portion and comprising a handle base wall extending within a plane and having an outer perimeter; and
   c. an outer upstanding wall, a portion of which extending from the head base wall towards the upper side of the cup support and at an angle to the plane of the head base wall so as to extend non-coplanar and non-parallel with the head base wall, wherein the outer upstanding wall extends around at least a portion of the outer perimeter of the head base wall, wherein the outer upstanding wall and the inner upstanding wall are laterally separated by the head base wall such that the head base wall, the inner upstanding wall, and the outer upstanding wall collectively define a trough adapted to contain a portion of the stream of liquid that impinges on the head portion.

2. The cup support of claim 1, wherein the head portion and the handle portion are integrally formed.

3. The cup support of claim 1, wherein the cup support is formed from a liquid absorbent material.

4. The cup support of claim 1, wherein the cup support is formed from a cellulose material.

5. The cup support of claim 1, wherein the outer upstanding wall extends around the entire outer perimeter of the head base wall.

6. The cup support of claim 1, wherein the outer upstanding wall angles laterally outwardly from the head base wall beyond the outer perimeter of the head base wall.

7. The cup support of claim 1, wherein the portion of the outer upstanding wall extends at an oblique angle to the plane of the head base wall.

8. The cup support of claim 1, wherein the outer upstanding wall and the inner upstanding wall extend at an angle relative to each other so as to be non-coplanar and non-parallel.

9. The cup support of claim 1, wherein the aperture opening comprises a substantially circular profile.

10. The cup support of claim 9, wherein the profile is a continuous circle.

11. The cup support of claim 1, wherein the outer upstanding wall comprises another portion that extends from the handle base wall towards the upper side of the cup support and at an angle to the plane of the handle base wall so as to extend non-coplanar and non-parallel with the handle base wall, wherein the outer upstanding wall extends around at least a portion of the outer perimeter of the handle base wall.

12. The cup support of claim 11, wherein the outer upstanding wall extends around the entire perimeter of the handle base wall.

13. The cup support of claim 1, wherein the plane of the head base wall and the plane of the handle base wall are substantially parallel.

14. The cup support of claim 1, wherein the plane of the head base wall and the plane of the handle base wall are substantially co-planar.

15. The cup support of claim 1, wherein the head base wall transitions into the handle base wall along a length of the cup support.

16. The cup support of claim 1, further comprising a rim extending laterally outwardly from an upper edge of the outer upstanding wall.

17. The cup support of claim 1, further comprising an upstanding support rib extending from the handle base wall towards the upper side of the cup support.

18. A cup support having an upper side and a lower side and comprising:
   a. a base wall extending within a plane and having an outer perimeter;
   b. an inner upstanding wall extending from the base wall towards the upper side of the cup support at an angle to the plane of the base wall so as to extend non-coplanar and non-parallel with the base wall, wherein the inner upstanding wall defines an aperture comprising an aperture opening configured to receive, in a direction from the upper side to the lower side of the cup support, a specimen cup for collection of a stream of liquid; and c. an outer upstanding wall extending from the base wall towards the upper side of the cup support and at an angle to the plane of the base wall so as to extend non-coplanar and non-parallel with the base wall, wherein the outer upstanding wall extends around at least a portion of the outer perimeter of the base wall and angles radially outwardly from the base wall beyond the outer perimeter of the base wall, wherein:
  the outer upstanding wall and the inner upstanding wall are laterally separated by the base wall such that the base wall, the inner upstanding wall, and the outer upstanding wall collectively define a trough adapted to contain a portion of the stream of liquid that impinges on the cup support; and
  the cup support is molded from a cellulose or polymeric material.

19. The cup support of claim 18, wherein the outer upstanding wall extends around the entire outer perimeter of the base wall.

\* \* \* \* \*